US012611279B2

(12) United States Patent　　　(10) Patent No.: US 12,611,279 B2
Robbins et al.　　　　　　　　　　(45) Date of Patent:　　　Apr. 28, 2026

(54) IN-LINE SUSPENSION ULTRASOUND ROLLSTAND

(71) Applicant: Bard Access Systems, Inc., Salt Lake City, UT (US)

(72) Inventors: Tab Robbins, Layton, UT (US); Matthew J. Prince, Herriman, UT (US); Paul T. Westwood, Kaysville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 445 days.

(21) Appl. No.: 17/687,443

(22) Filed: Mar. 4, 2022

(65) Prior Publication Data

US 2022/0280255 A1　　　Sep. 8, 2022

Related U.S. Application Data

(60) Provisional application No. 63/157,548, filed on Mar. 5, 2021.

(51) Int. Cl.
　　　*A61B 8/00*　　　　　(2006.01)
　　　*A61B 50/26*　　　　(2016.01)
　　　　　　　　(Continued)

(52) U.S. Cl.
　　CPC ............ *A61B 50/26* (2016.02); *A61B 8/4427* (2013.01); *A61B 8/462* (2013.01); *F16M 11/10* (2013.01);
　　　　　　　(Continued)

(58) Field of Classification Search
　　CPC ......... A61B 50/26; A61B 50/13; A61B 50/22; A61B 8/4427; A61B 8/462; A61B 8/461;
　　　　　　　　(Continued)

(56) References Cited

U.S. PATENT DOCUMENTS

2009/0198136 A1 *　8/2009　Yanagihara .............. A61B 8/14
　　　　　　　　　　　　　　　　　　　600/443
2011/0201927 A1 *　8/2011　Hayakawa ............... A61B 8/46
　　　　　　　　　　　　　　　　　　　600/437

(Continued)

FOREIGN PATENT DOCUMENTS

WO　　　2014/133605 A1　　9/2014

OTHER PUBLICATIONS

PCT/US2022/019011 filed Mar. 4, 2022 International Search Report and Written Opinion dated Jun. 14, 2022.

*Primary Examiner* — Michael J Carey
*Assistant Examiner* — Zainab Mohammed Aldarraji
(74) *Attorney, Agent, or Firm* — Rutan & Tucker LLP

(57) ABSTRACT

Disclosed herein is a system, apparatus and method directed to stabilizing a rollstand for an ultrasound system. The system, apparatus and method pertain to a rollstand comprising a base, an off-center vertical support, and an overhanging support for an ultrasound display of the ultrasound system. The off-center vertical support rises vertically from the base and is offset horizontally from a centroid of the base. A center of gravity of the rollstand may be located above the centroid of the base and above a vascular site of a patient being imaged by the ultrasound system. The overhanging support may be offset horizontally from the centroid of the base in a direction substantially opposite the off-center vertical support.

19 Claims, 8 Drawing Sheets

(51) Int. Cl.

| | |
|---|---|
| F16M 11/10 | (2006.01) |
| F16M 11/20 | (2006.01) |
| F16M 11/42 | (2006.01) |
| *F16M 11/14* | (2006.01) |

(52) U.S. Cl.
CPC ......... F16M 11/2021 (2013.01); F16M 11/42 (2013.01); *F16M 11/14* (2013.01); *F16M 2200/08* (2013.01)

(58) Field of Classification Search
CPC .. A61B 8/4405; F16M 11/10; F16M 11/2021; F16M 11/42; F16M 11/14; F16M 2200/08
See application file for complete search history.

(56) References Cited

U.S. PATENT DOCUMENTS

| | | | |
|---|---|---|---|
| 2014/0117635 A1* | 5/2014 | Ninomiya ............ | A61B 8/4405 |
| | | | 280/35 |
| 2015/0105660 A1* | 4/2015 | Ninomiya ............ | A61B 8/4427 |
| | | | 600/437 |
| 2017/0027541 A1* | 2/2017 | Henderson ........... | A61B 8/4405 |
| 2018/0368806 A1* | 12/2018 | Toyoda ................... | A61B 8/54 |

* cited by examiner

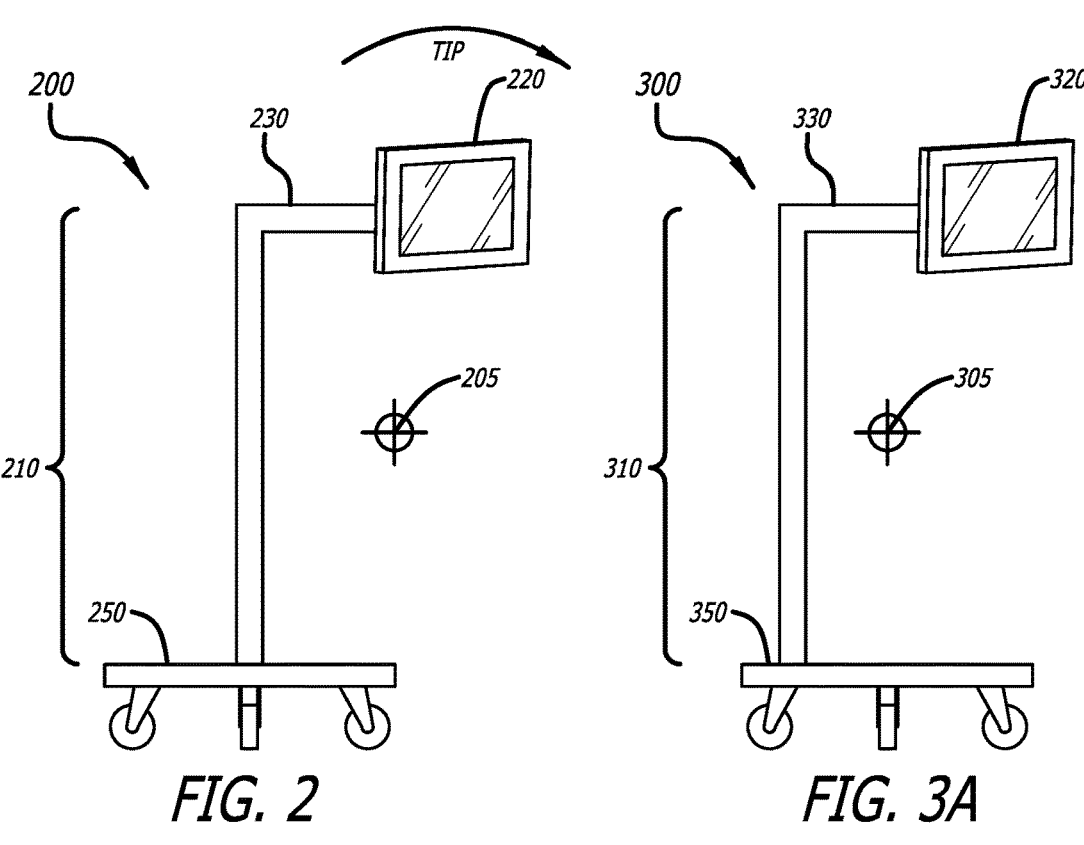
FIG. 2
FIG. 3A
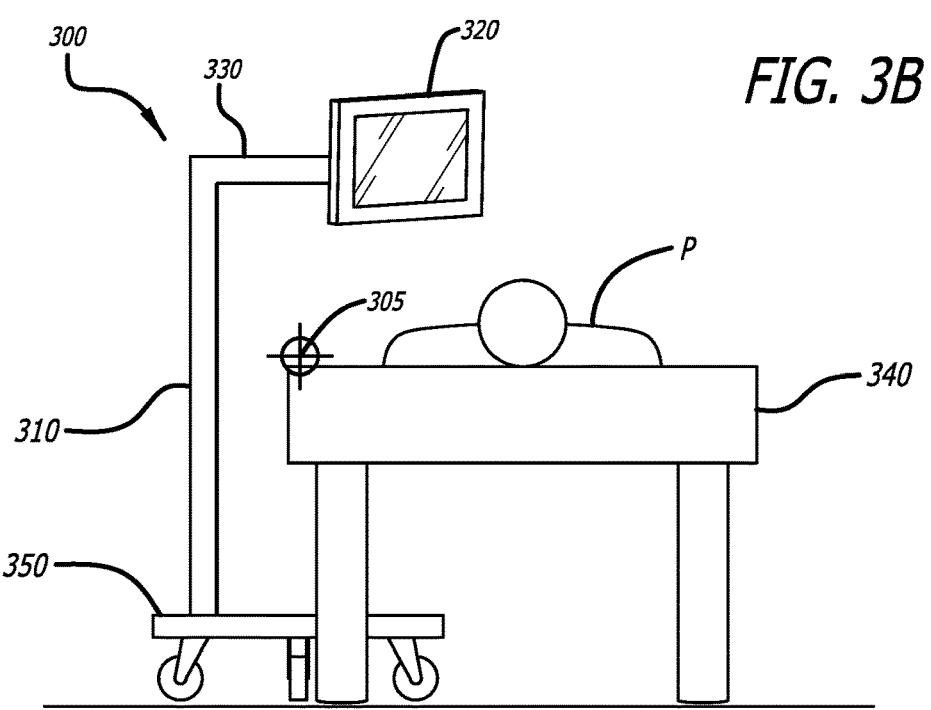
FIG. 3B 600
630
*FIG.6A*
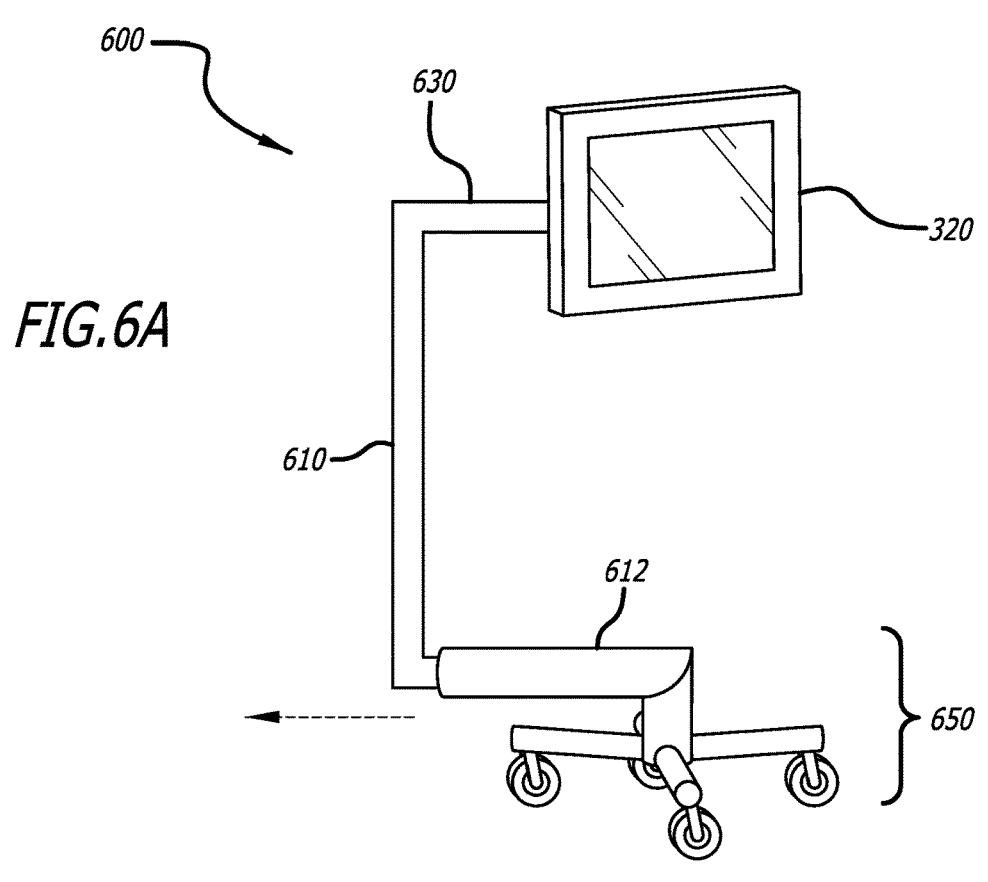
320
610
612
650
660
670
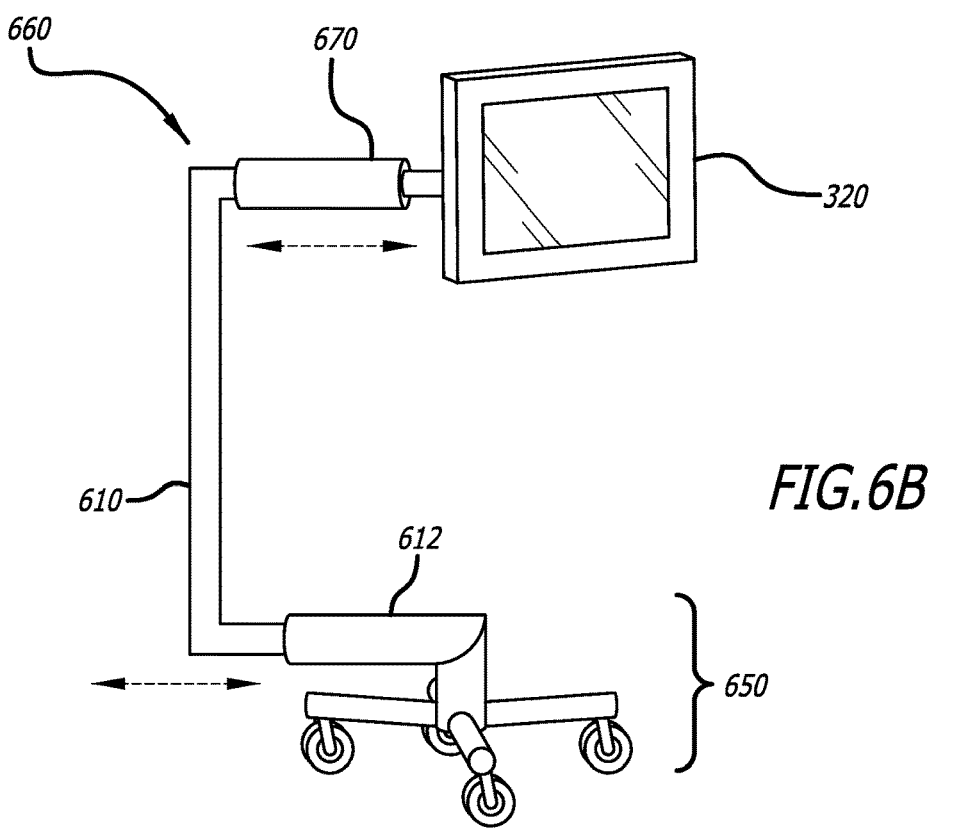
320
610
*FIG.6B*
612
650

800

810 — OBTAIN ROLL STAND

820 — POSITION ROLL STAND IN PROXIMITY TO PATIENT

830 — OPERATE PORTABLE ULTRASOUND SYSTEM

IN-LINE SUSPENSION ULTRASOUND ROLLSTAND

PRIORITY

This application claims the benefit of priority to U.S. Provisional Application No. 63/157,548, filed Mar. 5, 2021, which is incorporated by reference in its entirety into this application.

BACKGROUND

A common issue with portable ultrasound systems is that the need for stability to avoid tipping often constrains rollstand designs. A portable ultrasound system is typically placed on a rollstand that allows a clinician to move the portable ultrasound system within or between rooms, such as operating rooms, examination rooms, etc. The need for the ultrasound display screen to coincide with a clinician's standing or seated field of view results in the rollstand having a high center of gravity when carrying a portable ultrasound system. In some embodiments, a "high" center of gravity may refer to a center of gravity in an upper half of an object. In other embodiments, a "high" center of gravity may refer to a center of gravity in an upper third of an object. In yet other embodiments, a "high" center of gravity may refer to a center of gravity in an upper quarter of an object.

However, for patient and clinician safety it is important that the rollstand have a highly stable design to avoid tipping. In order to pass various safety tests, which may be specific to a manufacturer or a hospital, or may be an industry standard in some instances, existing ultrasound rollstands may locate the portable ultrasound system's center of gravity over a weighted base, and support the ultrasound system with a direct vertical support from the base to the elevated ultrasound position. Safety tests may vary in requirements and/or criteria; however, common criteria may include testing the stability of the ultrasound system and rollstand during transport, the stability of the ultrasound system and rollstand with unintentional movement (often tested on a surface at an incline), the force needed for movement, the stability of the ultrasound system and rollstand when passing over a threshold (e.g., a doorway), the stability of the ultrasound system and rollstand when static (often tested on a surface at an incline), etc. One exemplary set of technical standards for evaluating the safety and essential performance of medical electrical equipment is published by the International Electrotechnical Commission (IEC) and often referred to as the general standard IEC 60601. It is noted that other standards, tests or criteria may be utilized in determining the stability of a rollstand.

Another issue is the difficulty and complexity of interacting with an ultrasound display while also treating a patient, e.g., during a vascular access procedure. Ideally, the ultrasound system would be positioned directly above the patient's arm. However, existing rollstands typically support the ultrasound system with a vertical support such that the display of the ultrasound system is located directly above the base. Such a vertical support would be obstructed by the patient's bed, preventing the clinician from locating the ultrasound display close to the vascular access site. Instead, the rollstand is typically placed next to the bed or behind the clinician. As a result, clinicians must have great discipline while controlling their movements in a manner dissociated from the reference working visual. Accordingly, this procedure may take a great deal of attention and care to carry out. Furthermore, clinicians may experience ergonomic strain from twisting their backs and necks while performing multiple procedures in a typical day.

It would be advantageous to permit a broader population of nurses to practice the ultrasound-guided vascular access technique. Due to the separation detailed above between the ultrasound display and the vascular access site, and the difficulty of interacting with the ultrasound system while treating the patient, a vascular access procedure using a portable ultrasound system is traditionally a complex and difficult procedure to learn. As a result, only experienced and highly trained nurses can perform this procedure.

SUMMARY

Briefly summarized, embodiments disclosed herein are directed to systems, methods and apparatuses for portable ultrasound systems and stabilizing rollstands therefore to enable utilization of the portable ultrasound systems in close proximity to a patient bed.

Disclosed herein is a rollstand for a portable ultrasound system. The rollstand comprises a weighted base, an off-center vertical support, and an overhanging support for an ultrasound display of the portable ultrasound system. The off-center vertical support rises vertically from the weighted base and is offset horizontally from a centroid of the weighted base.

In some embodiments, a center of gravity of the rollstand is located above the centroid of the weighted base. In some embodiments, the overhanging support is offset horizontally from the centroid of the weighted base in a direction substantially opposite the off-center vertical support. In some embodiments, the center of gravity of the rollstand is located above a vascular site of a patient being imaged by the portable ultrasound system.

In some embodiments, the weighted base is positioned beneath a bed of the patient, and the vascular site is imaged by the portable ultrasound system. In some embodiments, the rollstand further comprises a boom arm. The overhanging support overhangs on the boom arm, and the boom arm comprises a pivot enabling the overhanging support to rotate about the boom arm. In some embodiments, the rollstand further comprises one or more pivots at one or more joints of the rollstand, including a boom arm pivot at a boom arm joint, an overhanging support pivot at an overhanging support joint, or a base pivot at a base joint. The boom arm pivot at the boom arm joint is configured to pivot a boom arm of the overhanging support. The overhanging support pivot at the overhanging support joint is configured to rotate the overhanging support in a plane of the overhanging support. The base pivot at the base joint is configured to raise or lower the weighted base.

In some embodiments, the weighted base comprises a stabilizing weight capable of balancing the overhanging support while the overhanging support extends away from the off-center vertical support. In some embodiments, the ultrasound display rests on the overhanging support. The ultrasound display has a reduced weight capable of being balanced by the off-center vertical support while the overhanging support extends away from the off-center vertical support. Also disclosed herein is a portable ultrasound system comprising a portable ultrasound display and a rollstand. The rollstand comprises a weighted base, an off-center vertical support, and an overhanging support for the ultrasound display. The off-center vertical support rises vertically from the weighted base and is offset horizontally from a centroid of the weighted base.

Also disclosed herein is a method of using a rollstand for a portable ultrasound system. The method comprises obtaining the rollstand. The rollstand comprises a weighted base, an off-center vertical support, and an overhanging support for an ultrasound display of the portable ultrasound system. The off-center vertical support rises vertically from the weighted base and is offset horizontally from a centroid of the weighted base. The method further comprises positioning the rollstand in proximity to a patient, wherein the ultrasound display rests on the overhanging support of the rollstand. The method further comprises operating the portable ultrasound system.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 2 illustrates a rollstand with a vertical center support and a boom arm coupled to a portable ultrasound system, according to some embodiments;

FIG. 3A illustrates a stable rollstand with an off-center vertical support for a portable ultrasound system, according to some embodiments;

FIG. 3B illustrates an exemplary usage of a stable rollstand with an off-center vertical support during an ultrasound-guided procedure, according to some embodiments;

FIGS. 6A-6B illustrate a stable rollstand with an extended horizontal offset distance, according to some embodiments;

DETAILED DESCRIPTION

Figure 1:
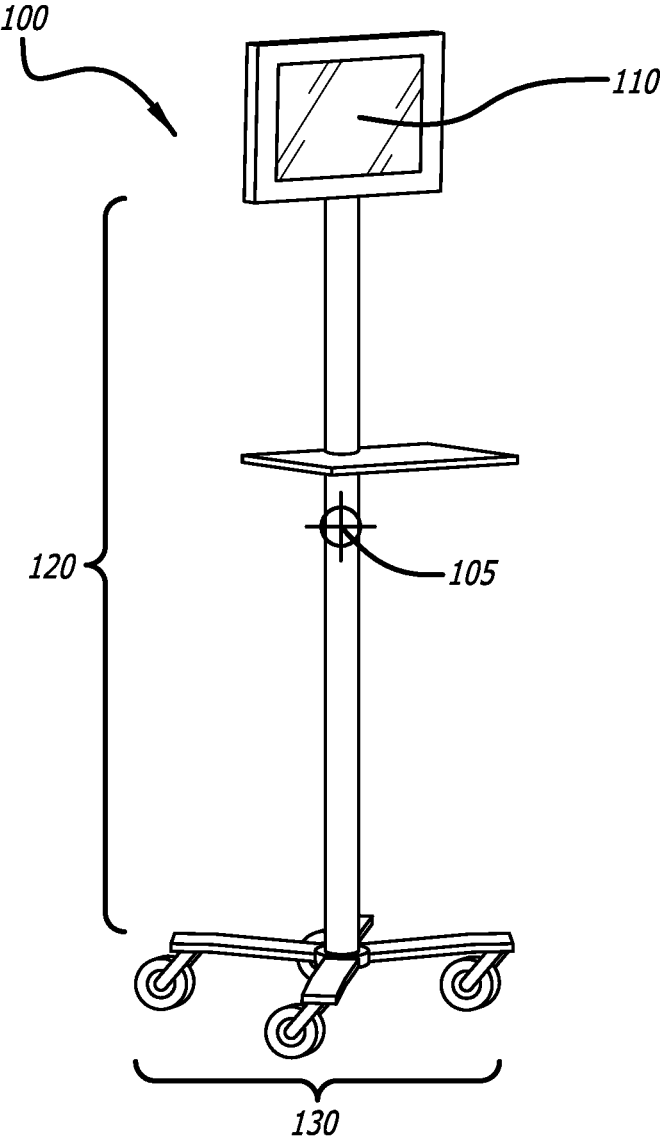
FIG. 1 illustrates an exemplary rollstand for a portable ultrasound system.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions.

Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Referring to FIG. 1, an exemplary conventional rollstand 100 for a portable ultrasound system 110 is shown. A portable ultrasound system 110 is typically placed on a conventional rollstand 100 that allows a clinical user to move the portable ultrasound system within or between rooms, such as operating rooms, examination rooms, etc. The conventional rollstand 100 may be wheeled to the desired location, and then remains stably in that location while the clinical user performs a procedure, such as a vascular access for insertion of a catheter, with the aid of ultrasound system 110.

Conventional rollstand 100 includes a vertical support 120 and a stable wheelbase 130, which may be weighted. Portable ultrasound system 110 is positioned on a support, such as a stand, rack, bracket, or backplate, at the top of vertical support 120, enabling the clinician to view the ultrasound system's display in a hands-free manner. The ultrasound system 110 may be lightweight (e.g., approximately 2 lbs.) and may comprise a single main terminal with an LCD display, touchscreen, motherboard, USB ports, battery or other power source, and/or any other components needed to operate the ultrasound system 110. Furthermore, ultrasound system 110 may include a separate ultrasound probe connected to the main terminal and used to emit ultrasound energy to image a patient site, such as a blood vessel.

Portable ultrasound system 110 is positioned at the top of the rollstand 100, so as to coincide with a clinician's standing or seated field of view. However, for patient and clinician safety, it is important for the rollstand to be highly stable against tipping. In order to pass safety tests as noted above, conventional rollstand designs, such as rollstand 100, may therefore locate the center of gravity 105 of the rollstand 100 over a weighted base, such as wheelbase 130, respectively, in order to best avoid tipping. Such designs may moreover support the ultrasound system with a direct vertical support, such as vertical support 120, from the weighted base to the elevated ultrasound position.

While the clinician performs an ultrasound-assisted procedure, such as a vascular access, the ultrasound system ideally should be positioned directly over the target insertion site of the procedure, such as the patient's arm. However, conventional rollstand 100 support the ultrasound system with direct vertical support 120 from the base to the elevated position of the ultrasound system's display. Such vertical support 120 are obstructed by the patient's bed, preventing the clinician from positioning the ultrasound display close to the vascular access site. Instead, the conventional rollstands are placed next to the bed or behind the clinician.

As a result of this separation of the ultrasound system from the vascular access site, clinicians must have great discipline while controlling their movements in a manner dissociated from the reference working visual, and the procedure may take a great deal of attention and care to carry out. Furthermore, clinicians may experience ergonomic strain from twisting their backs and necks while performing multiple procedures in a typical day.

The disclosed apparatus, system, and methods can address these issues. In particular, the disclosed rollstand can be positioned close enough to a patient bed to enable a clinician to interact easily with both the ultrasound display screen and insertion site, while the disclosed rollstand remains highly stable. Moreover, the disclosed apparatus, system, and methods enable a broader population of nurses to perform vascular access procedures with a portable ultrasound system, by considerably simplifying the required tasks.

Referring now to FIG. 2, an illustration of a rollstand having a boom arm with a display of an ultrasound system connected at a distal end of the boom arm is shown in accordance with some embodiments. FIG. 2 depicts a rollstand 200 having a boom arm 230 that extends distally from a vertical support 210, where the vertical support 210 extends vertically from the cetern of the wheelbase 250. In particular, the rollstand 200 illustrates a scenario in which tipping would likely occur due to the center of gravity 205 of the rollstand being over an edge of the wheelbase 250. As a result, the weight of the rollstand 200 is shifted to one side thereby increasing the likelihood that the rollstand 200 will tip. Thus, although the rollstand 200 provides an improved design and improved functionality over the rollstand 100 of FIG. 1 as the rollstand 200 may provide some ability for the wheelbase 250 to be located under a patient's bed while the ultrasound system 220 is located in view of a clinician, the rollstand 200 is unlikely to pass various safety requirements due to the increased likelihood of tipping. Therefore, improvements rollstands 100 and 200 are needed.

Referring now to FIG. 3A, a stable rollstand 300 with an off-center vertical support 310 for a portable ultrasound system 320 is shown according to some embodiments. Fore example, ultrasound system 320 can rest on an overhanging support (such as a stand, rack, bracket, or backplate), suspended at a distal end of a boom arm 330, which is configured to extend over a patient's bed 340 (see FIG. 3B). Boom arm 330 extends away from off-center vertical support 310. Rollstand 300 further includes wheelbase 350, which enables the rollstand 300 to be moved within or between rooms, such as operating rooms, examination rooms, etc. The boom arm 330 may alternatively be referred to as a C-arm.

Further, wheelbase 350 is configured for placement beneath patient bed 340, while portable ultrasound system 320 is positioned in proximity to bed 340 and the patient P. In the embodiment of FIGS. 3A-3D, as the off-center vertical support 310 is horizontally offset from the center of wheelbase 350, vertical support 310 is not obstructed by patient bed 340 while wheelbase 350 is beneath the bed. In addition, because boom arm 330 overhangs bed 340, the ultrasound system 320 can be positioned substantially closer to the site of the ultrasound-guided procedure than with conventional rollstands. In some embodiments, the ultrasound system 320 may be secured to the boom arm 330 by securing means, such as a backplate, bracket, rack, and/or a bolt. Wheelbase 350 will be alternatively referred to herein as a wheelbase or a base.

Unlike the vertical supports 120 and 210 of FIGS. 1-2, off-center vertical support 310 is horizontally offset from the center of wheelbase 350. In particular, the center of gravity of rollstand 300 may be over wheelbase 350, because off-center vertical support 310 is weighted to lower the center of gravity of the rollstand 300 having ultrasound system 320 coupled thereto compared to the illustration of FIG. 1. In particular, the weight of the off-center vertical support 310 is offset in the opposite direction from the boom arm 330 and ultrasound system 320. That is, the boom arm 330 and ultrasound system 320 are horizontally offset in a first direction from the center of the wheelbase 350, and the off-center vertical support 310 is horizontally offset in the substantially opposite direction, resulting in a balanced, stable, centrally-located center of gravity 305. In particular, maintaining the center of gravity 305 over wheelbase 350 enables the rollstand 300 to maintain stability, thereby solving the problem of an increased likelihood of tipping as discussed with respect to FIG. 2.

In some embodiments, the boom arm 330 and ultrasound system 320 may be lighter than vertical support 310 (e.g., have a lower total mass), the boom arm 330 and the ultrasound system 320 may be horizontally offset farther away from wheelbase 350 than is vertical support 310, while still maintaining the center of gravity 305 over the center of the wheelbase 350. For example, the off-center vertical support 310 may be horizontally offset approximately 5 cm to 20 cm from the center of wheelbase 350, while the boom arm 330 may extend approximately 20 cm to 80 cm in the opposite direction. As a result, it is possible for the center of gravity 305 to be located directly above the vascular access site, while the vascular access procedure is performed.

To further stabilize the rollstand 300, base 350 may be weighted. In some embodiments, base 350 and/or off-center vertical support 310 may be weighted, in order to improve the balance of the rollstand 300 (including the boom arm 330 and ultrasound system 320). In a typical embodiment, the ultrasound system 320 may weigh approximately two pounds (2 lbs.). In some embodiments, the ultrasound system may weigh less than two pounds.

FIG. 3B illustrates usage of the stable rollstand 300 of FIG. 3A with an off-center vertical support during an ultrasound-guided procedure, according to some embodiments. In this example, rollstand 300 is positioned close to bed 340 and patient P for usage during a procedure, such as a vascular access procedure. As shown, a portion of the wheelbase 350 is be positioned beneath the bed 340, while the off-center vertical support 310 supports the boom arm 330 and the ultrasound system 320 without being obstructed by bed 340. At the same time, boom arm 330 extends over the bed 340, so that ultrasound system 320 can be suspended in close proximity to patient P. For example, ultrasound system 320 can be suspended directly over the vascular access site, such as the insertion site of a needle in the arm or chest of patient P. As a result, the clinician is able to perform the vascular access, or other ultrasound-guided procedure, with easy access to the reference working visual, and without having to strain to view display 320 as described above with respect to FIG. 1.

Figure 3C:
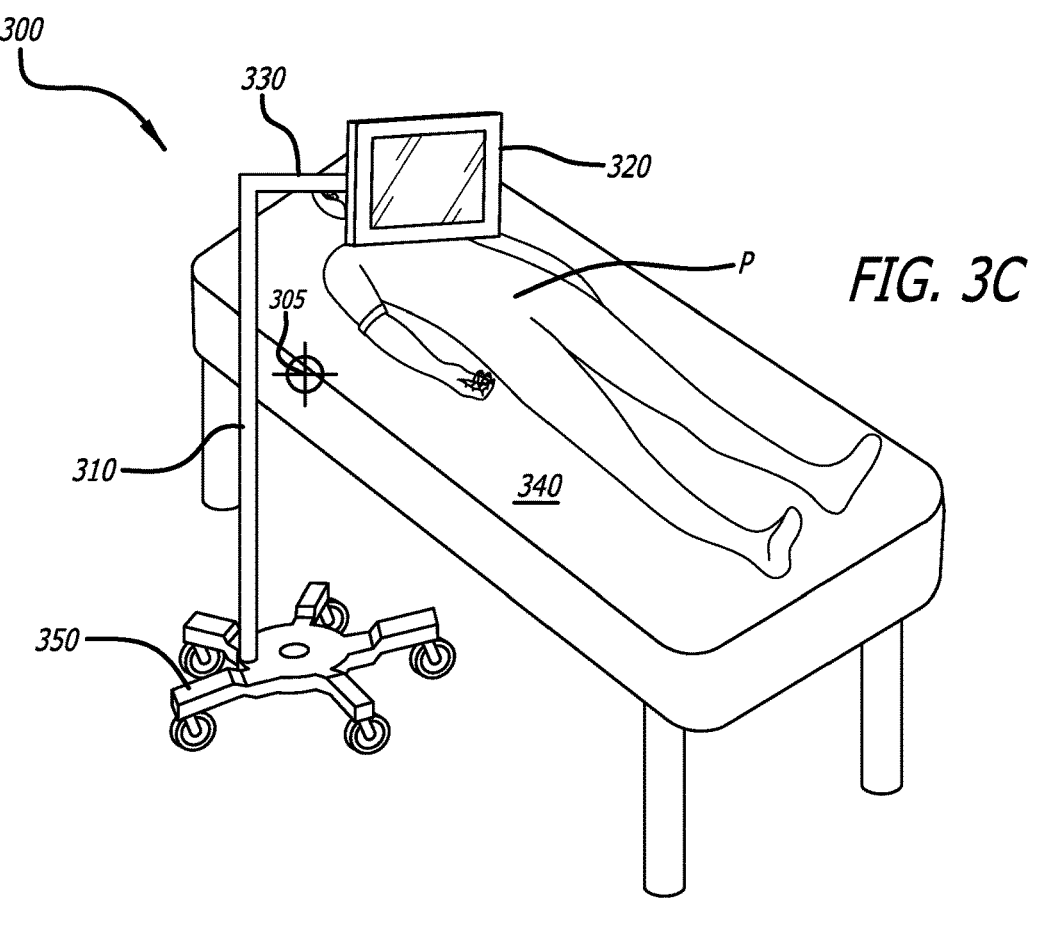
FIG. 3C illustrates the center of gravity of the stable rollstand with an off-center vertical support of FIG. 3A during an ultrasound-guided procedure, according to some embodiments.

FIG. 3C illustrates the center of gravity 305 of the stable rollstand with an off-center vertical support of FIG. 3A during an ultrasound-guided procedure, according to some embodiments. As shown, center of gravity 305 can be directly above the wheelbase 350 of rollstand 300, and can be close to the patient P and/or to the site of the vascular access procedure being performed on patient P. For example, as the wheelbase 350 is moved further under the bed 340, the center of gravity 305 may be placed directly over the vascular access site, such as the insertion site of a needle in the arm 360 or chest of patient P.

As illustrated in FIG. 3C, the off-center vertical support is offset in an opposite horizontal direction from the boom arm 330 and ultrasound system 320, the center of gravity 305 is centrally-located over wheelbase 350. That is, the boom arm 330 and ultrasound system 320 are horizontally offset in a first direction from wheelbase 350 (left in the example of FIG. 3C), and the off-center vertical support 310 is horizontally offset in the substantially opposite direction (right in this example), resulting in center of gravity 305 being located over wheelbase 350. This central location of center of gravity 305, in turn, balances and stabilizes rollstand 300 to avoid tipping.

Figure 3D:
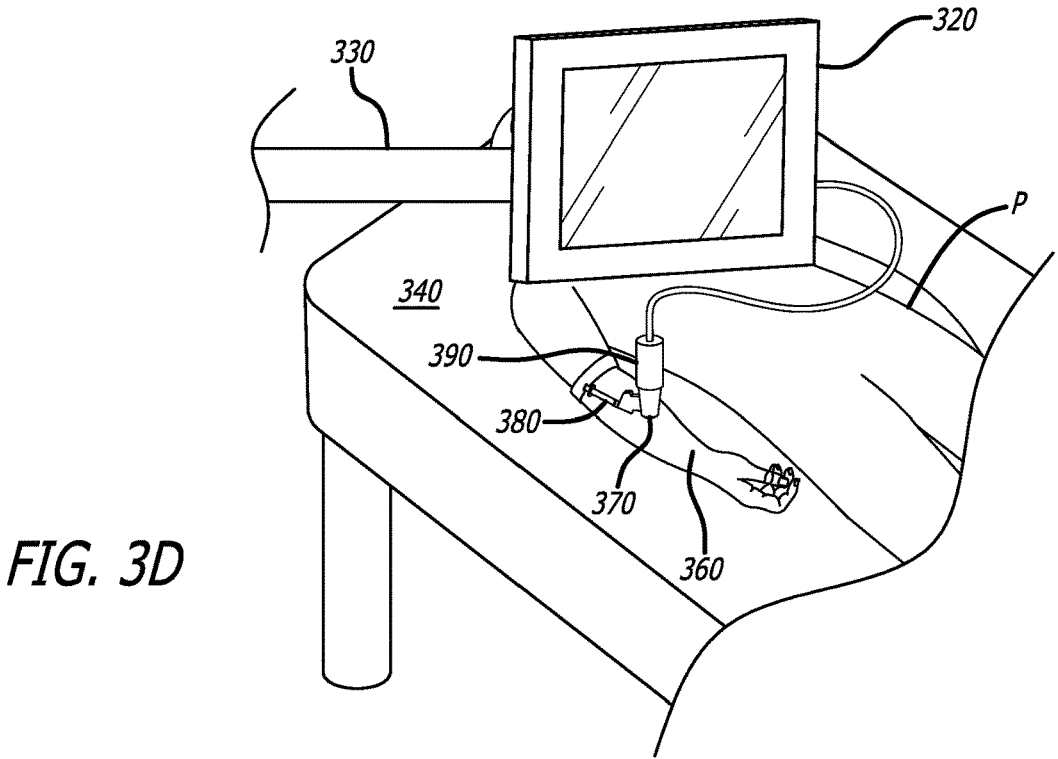
FIG. 3D illustrates an second exemplary usage of a portable ultrasound system positioned on a stable rollstand with an off-center vertical support, according to some embodiments.

FIG. 3D illustrates usage of a portable ultrasound system 320 positioned on the stable rollstand 300 with an off-center vertical support, according to some embodiments. In this example, ultrasound system 320 is resting on the overhanging support (not shown) at the end of boom arm 330 of the disclosed stable rollstand. Portable ultrasound terminal and display 320 is positioned in close proximity to insertion site 370 of needle 380 for vascular access in patient arm 360, for example to insert a peripherally inserted central catheter (PICC) in arm 360. Portable ultrasound terminal 320 may be connected to ultrasound probe 390, which a clinician can position over insertion site 370 to scan the patient's blood vessels or internal organs.

Because the rollstand can maintain its stability when its wheelbase is positioned beneath the patient's bed and the boom arm 330 and overhanging support extend over the bed, a clinician can make use of the ultrasound terminal 320 in close proximity to vascular access site 370. Accordingly, the disclosed rollstand can significantly simplify the use of a portable ultrasound system for a vascular access or other procedure, relieve clinician ergonomic strain, and enable a broader population of clinicians to perform the ultrasound guided vascular access technique.

Figure 4A:
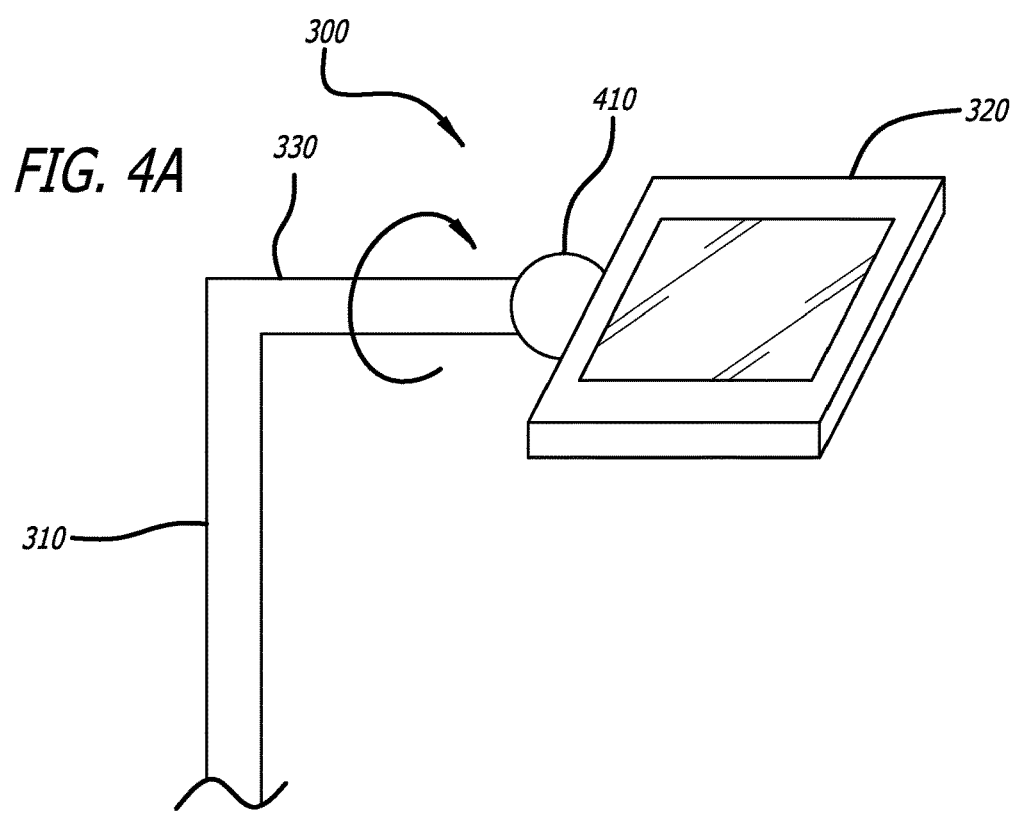
FIG. 4A illustrates a stable rollstand with a reversible pivoting ultrasound stand, according to some embodiments.

FIG. 4A illustrates a stable rollstand with a reversible pivoting ultrasound stand, according to some embodiments. In an embodiment, rollstand 300 can have a pivot 410 at the joint connecting the overhanging support, which holds ultrasound system 320, to boom arm 330. Pivot 410 can allow the overhanging support and ultrasound system 320 to be rotated by 180°, or even 360°, about the axis of boom arm 330. This allows the rollstand 300 to be oriented with the off-center vertical support 310 to either the clinician's left or right sides, while the ultrasound system 320 faces the clinician.

Figure 4B:
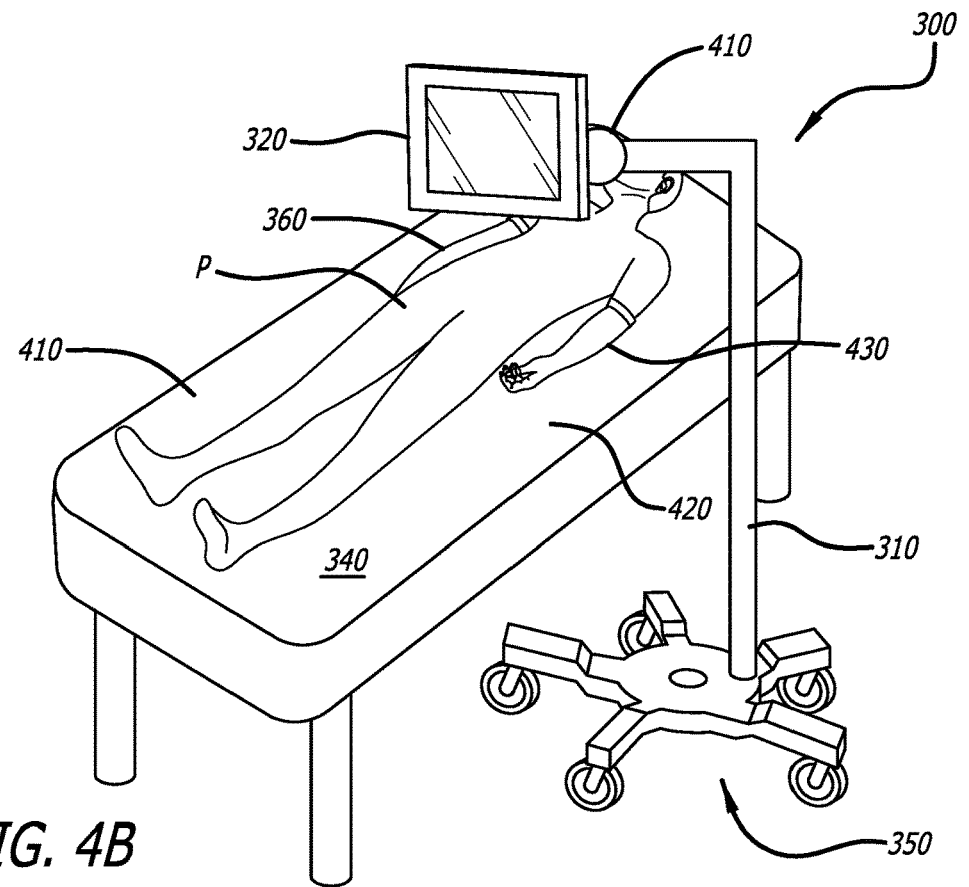
FIG. 4B illustrates usage of a stable rollstand with a reversible pivoting ultrasound stand during an ultrasound-guided procedure, according to some embodiments.

FIG. 4B illustrates usage of a stable rollstand with a reversible pivoting ultrasound stand during an ultrasound-guided procedure, according to some embodiments. As described above, pivot 410 can allow the overhanging support and ultrasound system 320 to be rotated about the axis of boom arm 330. Accordingly, rollstand 300 can be positioned to either side of patient P while the ultrasound system 320 faces the clinician.

In the example of FIGS. 3A-3B, rollstand 300 is positioned to a left side 410 of patient bed 340 for a vascular access procedure to the left arm 360 of patient P. By contrast, in the example of FIG. 4B, rollstand 300 is positioned to a right side 420 of bed 340. In both cases, ultrasound system 320 has the same orientation. As a result, the clinician can work from either the left 410 or right 420 sides of bed 340, while still positioning rollstand 300 in close proximity to the vascular access site (or any other site being imaged by the portable ultrasound system) on patient P. In particular, the clinician can position rollstand 300 close to a vascular access site on either left arm 360 or right arm 430 of patient P, while simultaneously being able to use portable ultrasound system 320 and reach the vascular access site comfortably.

In various embodiments, the disclosed stable rollstand 300 with off-center vertical support may have other hinges and/or pivots at various joints, or other structural variations, as described below in the examples of FIGS. 5A-6.

Figures 5A, 5B:
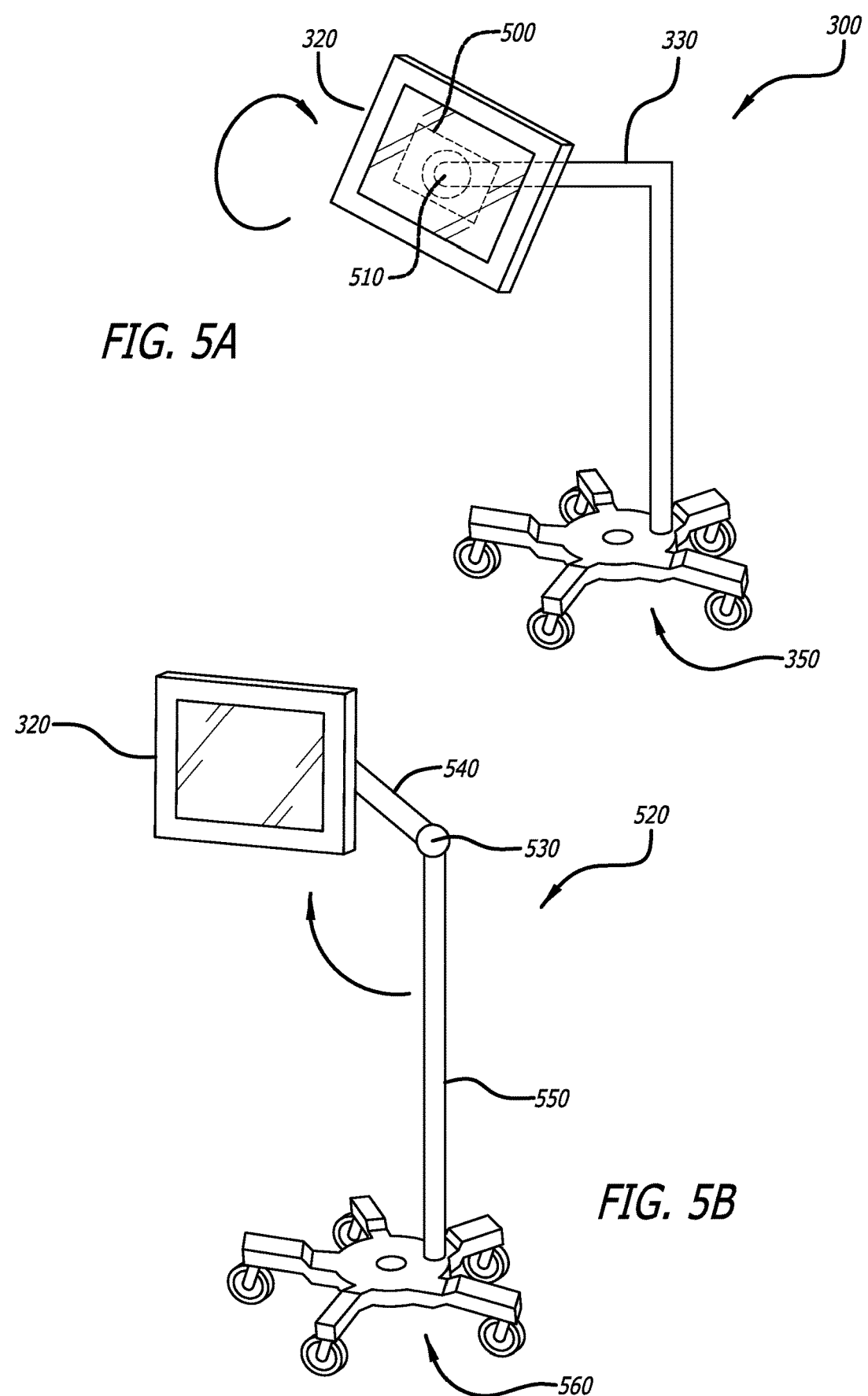
FIG. 5A illustrates a stable rollstand with a pivoting ultrasound stand, according to some embodiments.
FIG. 5B illustrates a stable rollstand with a pivoting boom arm, according to some embodiments.

FIG. 5A illustrates a stable rollstand with a pivoting ultrasound stand, according to some embodiments. In some embodiments, the rollstand includes a boom arm pivot 510 that couples the ultrasound system 320 to the boom arm 330. As illustrated, a bracket 500 may be coupled to the backside of the ultrasound system 320 and be configured to receive or house the pivot 510, which is in turn configured to couple to the distal end of the boom arm 300. Using the boom arm pivot 510, the ultrasound system 320 may be rotated among multiple degrees of freedom.

FIG. 5B illustrates a stable rollstand with a pivoting boom arm, according to some embodiments. In this example, the rollstand 520 has a boom arm pivot 530 at a joint between the boom arm 540, off-center vertical support 550 and a wheelbase 560. The boom arm pivot 530 can pivot the boom arm 540 in particular degrees of freedom, which enables the rollstand 520 to accommodate varying heights (e.g., varying heights sides of a patient bed, varying positions of the patient bed (such as at a partial incline), varying heights of portions of the patient (e.g., larger stomach, larger chest, etc.)).

In some embodiments, the boom arm pivot 530 may be a multi-directional swiveling joint, allowing the boom arm 320 to be swiveled with two angular degrees of freedom. That is, boom arm pivot 530 may enable the boom arm 540 and/or the ultrasound system 320 to be repositioned along a spherical surface, or a portion thereof. Alternatively, in some embodiments, the boom arm pivot 530 has only one angular degree of freedom, but the off-center vertical support 310 also rotates about its own axis. In this case, the combination of the boom arm pivot 530 and the rotation of the off-center vertical support 310 also provides two degrees of freedom to reposition ultrasound system 320 along a spherical shell.

In some embodiments, the boom arm pivot 510 of FIG. 5A can be used in combination with the boom arm pivot 530. For example, the clinician may rotate ultrasound system 320 using the boom arm pivot 510 in order to compensate for pivoting the boom arm 320, thereby effectively changing the height and positioning of ultrasound system 320, while retaining its level orientation.

FIG. 6A illustrates a stable rollstand 600 with an extended horizontal offset distance, according to some embodiments. In some embodiments, a horizontal linking element 612 that joins the bottom of off-center vertical support 610 to the wheelbase 650 can telescope or extend, thereby increasing the horizontal offset of off-center vertical support 610, while maintaining stability of rollstand 600. This feature may allow the rollstand 600 to be used with the vertical support 610 that is offset over a varying horizontal distance, for example next to a particularly large patient bed or other large furniture, or when the patient vascular access site is particularly far from the edge of the bed. FIG. 6B illustrates an alternative embodiment to that of FIG. 6A in which a stable rollstand 660 includes the functionality to extend at either or both of the bottom or top of the off-center vertical support 610. In the example embodiment illustrated, the rollstand 660 includes the horizontal linking element 612 of FIG. 6A in an extended position and includes an extendable boom arm 670 that is configured to telescope or extend in one or either direction as illustrated (where the extendable boom arm 670 is configured to operate in the same manner as the extension of the horizontal linking element 612 shown between FIGS. 6A-6B). Based on the weight of the components of the rollstand 660 (including the ultrasound system 320), the extendability of the horizontal linking element 612 and the extendable boom arm 670 may be restricted accordingly during manufacture.

Figure 7A:
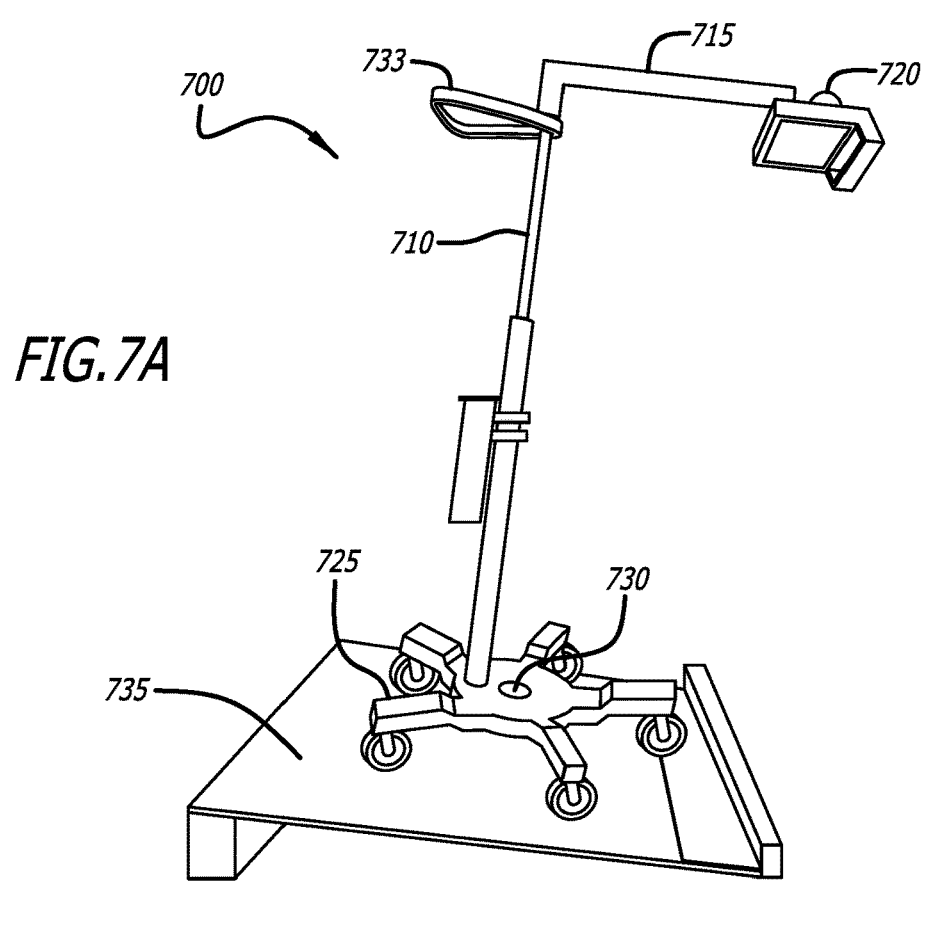
FIG. 7A illustrates stability of a rollstand with an off-center vertical support for a portable ultrasound system, according to some embodiments.

FIG. 7A illustrates stability of a rollstand 700 with an off-center vertical support 710 for a portable ultrasound system, according to some embodiments. In this example, rollstand 700 includes off-center vertical support 710, boom arm 715, overhanging stand 720, and wheelbase 725.

As shown, off-center vertical support 710 is located away from the center 730 of wheelbase 725. Boom arm 715 and overhanging stand 720 extend beyond the edge of wheelbase 725, enabling a clinician to position the ultrasound display in close proximity to the vascular access site, for example directly over the access site, while the wheelbase 725 is under the patient's bed. Boom arm 715 and overhanging stand 720 are balanced by off-center vertical support 710 (i.e., due to the weight of the wheelbase 725 and location thereof relative to the overhanging stand 720 and the display coupled thereto), thereby maintaining the center of gravity of rollstand 700 over wheelbase 725 for stability. In particular, in various embodiments, the center of gravity of rollstand 700 may be located over center 730 of wheelbase 725, or over another location on wheelbase 725. In some embodiments, boom arm 715 and overhanging stand 720 can be further balanced by weighted arm 733, thereby further stabilizing rollstand 750.

As shown, rollstand 700 is placed on a ramp 735, demonstrating its stability against tipping. Despite being steeply inclined on ramp 735, rollstand 700 remains stable and upright. In some embodiments, the center of gravity of rollstand 700 may be located over wheelbase 725 even while rollstand 700 is tilted, as shown. In some embodiments, the center of gravity of rollstand 700 may continue to be located over, or nearly over, the center 730 of wheelbase 725 even while rollstand 700 is tilted.

Figure 7B:
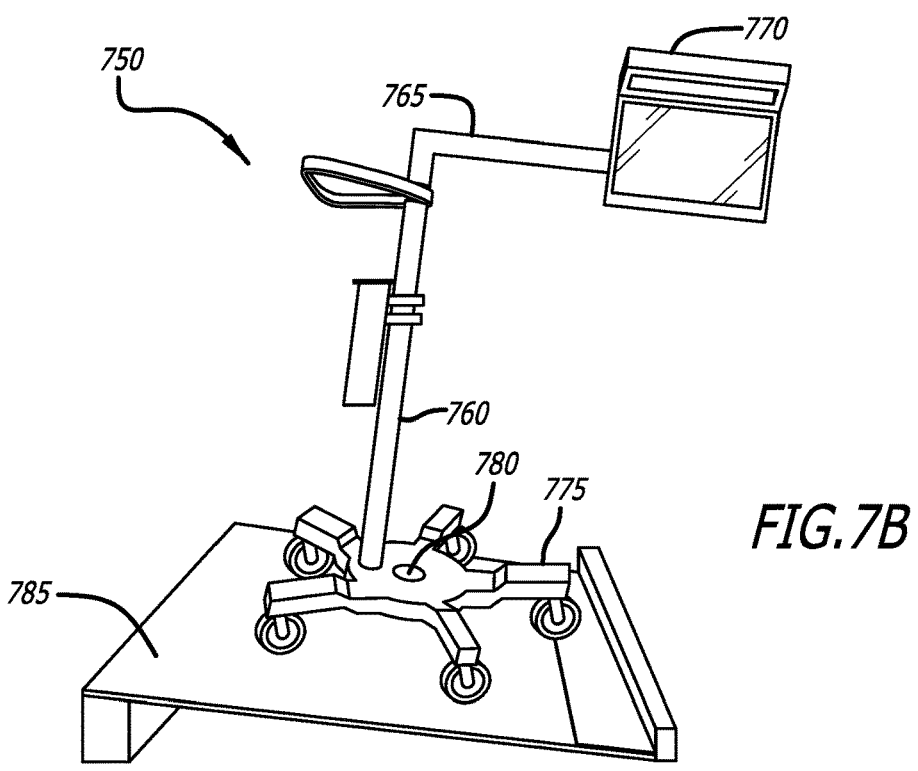
FIG. 7B illustrates usage of a stable rollstand with an off-center vertical support for a portable ultrasound system, according to some embodiments.

FIG. 7B illustrates usage of a stable rollstand 750 with an off-center vertical support 760 for a portable ultrasound system, according to some embodiments. In this example, rollstand 750 includes off-center vertical support 760, boom arm 765, an overhanging stand holding ultrasound display 770, and wheelbase 775.

As shown, off-center vertical support 760 is located away from the center 780 of wheelbase 775. Boom arm 765 and the overhanging stand extend beyond the edge of wheelbase 775, enabling a clinician to position ultrasound display 770 in close proximity to the vascular access site.

Boom arm 715, the overhanging stand, and the additional weight and torque of ultrasound display 770 are balanced by off-center vertical support 760 (i.e., due to the weight of the wheelbase 775 and location thereof relative to the overhanging stand 720 and the display coupled thereto), thereby maintaining the center of gravity of rollstand 750 over wheelbase 775 for stability. In particular, in some embodiments, the center of gravity of rollstand 750 may be located over the center 780 of wheelbase 775.

As shown, rollstand 750 is placed on a ramp 785, demonstrating its stability against tipping. Despite being steeply inclined on ramp 785, rollstand 750 remains stable and upright. In some embodiments, the center of gravity of rollstand 750 may be located over wheelbase 775 even while rollstand 750 is tilted, as shown.

11

Figure 8:
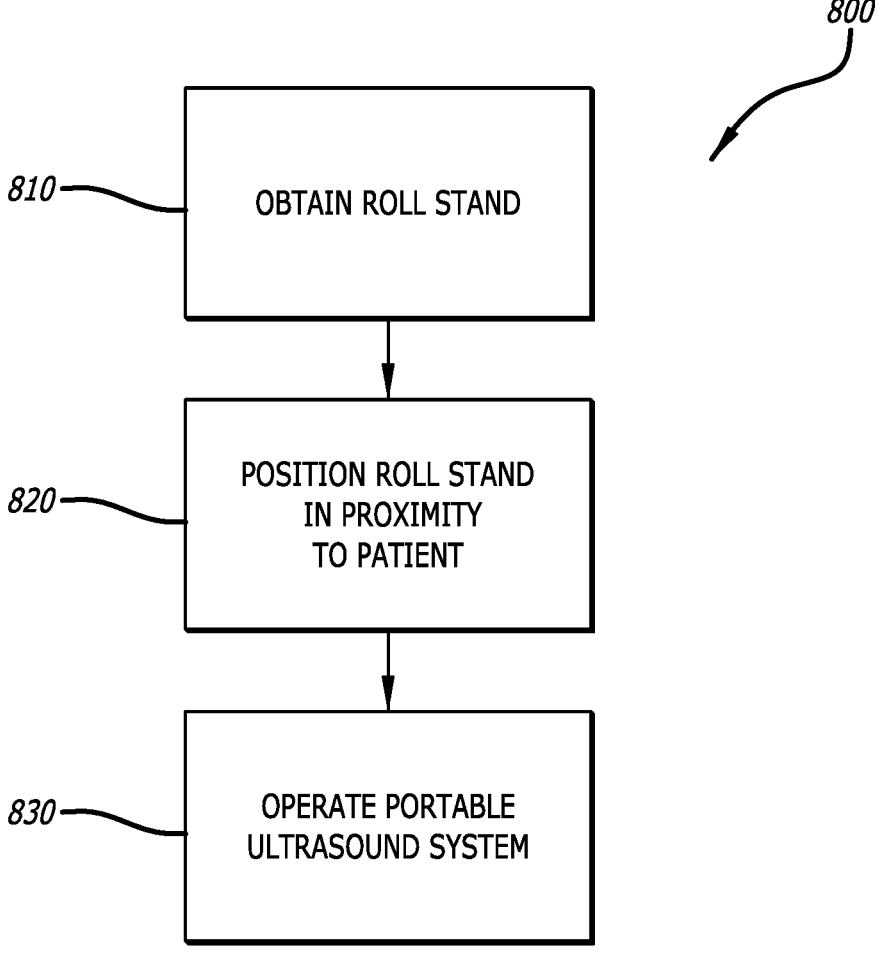
FIG. 8 illustrates a method of using a rollstand with an off-center vertical support for a portable ultrasound system, according to some embodiments.

FIG. 8 illustrates a flowchart of a method 800 of using a rollstand with an off-center vertical support for a portable ultrasound system, according to some embodiments. Each block illustrated in FIG. 8 represents an operation performed in the method 800 of using a rollstand with an off-center vertical support for a portable ultrasound system. In various embodiments, the method can be performed by one or more users, such as nurses, doctors, or other clinicians, etc.

As an initial step in the method 800, the user can obtain the rollstand (block 810). The rollstand comprises a wheelbase, an off-center vertical support, and an overhanging support for an ultrasound display screen of the portable ultrasound system. The wheelbase may be weighted so as to lower the center of gravity and improve stability of the rollstand. The off-center vertical support rises vertically from the wheelbase and is offset horizontally from a centroid of the wheelbase.

Next, the user can position the rollstand in proximity to a patient (block 820) while performing a procedure guided by the ultrasound system, such as a vascular access procedure. In an embodiment, the wheelbase of the rollstand may fit beneath the patient's bed. The off-center vertical support and overhanging support may then enable the portable ultrasound system, which may rest on the overhanging support, to be positioned in proximity to the patient and the vascular access site. In various embodiments, the rollstand can be positioned to a left side of the patient bed, e.g. for a vascular access procedure to the patient's left side, or to a right side of the patient bed for a procedure to the patient's right side. In either case, the ultrasound display can be rotated so as to be oriented toward the clinical user, enabling the clinical user to work from either the left or right sides of the patient's bed.

Finally, the user can operate the portable ultrasound system (block 830). Accordingly, the clinical user can make use of the ultrasound system in close proximity to the vascular access site, thereby simplifying the procedure, relieving ergonomic discomfort and strain for the clinical user, and enabling a broader population of clinicians to perform the ultrasound guided vascular access technique.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rollstand for an ultrasound system, comprising:
a base including a plurality of wheels;
an off-center vertical support rising vertically from the base and offset in a first horizontal direction from a centroid of the base;
an overhanging support extending distally from the off-center vertical support in a second horizontal direction that is oriented opposite with respect to the first horizontal direction, wherein the overhanging support is configured to couple with an ultrasound display of the ultrasound system; and
a boom arm extending in the second horizontal direction between the off-center vertical support and the overhanging support, the boom arm including a pivot that enables the overhanging support to rotate about a longitudinal axis of the boom arm,

12 wherein:
the off-center vertical support is coupled to the base via a horizontal linking element, the horizontal linking element extends in line with the first horizontal direction such that the off-center vertical support is located off-set from the centroid of the base in the first horizontal direction and in line with the horizontal linking element, and
the off-center vertical support is horizontally and linearly displaceable with respect to the base in line with the first horizontal direction.

2. The rollstand of claim 1, wherein a center of gravity of the rollstand is located over the centroid of the base.

3. The rollstand of claim 2, wherein the overhanging support is offset horizontally from the centroid of the base at a distal edge of the base.

4. The rollstand of claim 2, wherein the rollstand is configured such that the center of gravity of the rollstand is located directly over a vascular site of a patient during imaging with the ultrasound system.

5. The rollstand of claim 4, wherein the base is configured to be located beneath a bed of the patient during imaging of the vascular site by the ultrasound system.

6. The rollstand of claim 1, further comprising one or more pivots at one or more joints of the rollstand including:
a boom arm pivot at a boom arm joint configured to pivot the boom arm of the overhanging support,
an overhanging support pivot at an overhanging support joint configured to rotate the overhanging support in a plane of the overhanging support, or
a base pivot at a base joint configured to raise or lower the base.

7. The rollstand of claim 1, wherein the base includes a stabilizing weight configured to balance a weight of the overhanging support while the overhanging support extends away from the off-center vertical support.

8. The rollstand of claim 1, wherein the ultrasound display:
rests on the overhanging support, and
has a weight configured to balance a weight of the off-center vertical support while the overhanging support extends away from the off-center vertical support.

9. An ultrasound system, comprising:
an ultrasound display; and
a rollstand, the rollstand including:
a base including a plurality of wheels,
an off-center vertical support rising vertically from the base and offset in a first horizontal direction from a centroid of the base,
an overhanging support extending away from the off-center vertical support in a second horizontal direction that is oriented opposite with respect to the first horizontal direction, wherein the overhanging support is configured to couple with the ultrasound display; and
a boom arm extending in the second horizontal direction between the off-center vertical support and the overhanging support, the boom arm including a pivot that enables the overhanging support to rotate about a longitudinal axis of the boom arm,
wherein:
the off-center vertical support is coupled to the base via a horizontal linking element, the horizontal linking element extends in line with the first horizontal direction such that the off-center vertical support is located off-set from the centroid of the base in the first horizontal direction and in line with the horizontal linking element, and the off-center vertical support is horizontally and linearly displaceable with respect to the base in line with the first horizontal direction.

10. The ultrasound system of claim 9, wherein a center of gravity of the rollstand is located over the centroid of the base.

11. The ultrasound system of claim 10, wherein the overhanging support is offset horizontally from the centroid of the base at a distal edge of the base.

12. The ultrasound system of claim 10, wherein the rollstand is configured such that the center of gravity of the rollstand is located above a vascular site of a patient during imaging with the ultrasound system.

13. The ultrasound system of claim 12, wherein the base is configured to be located beneath a bed of the patient during imaging of the vascular site by the ultrasound system.

14. The ultrasound system of claim 9, wherein the rollstand further comprises one or more pivots at one or more joints of the rollstand including:

a boom arm pivot at a boom arm joint configured to pivot the boom arm of the overhanging support, an overhanging support pivot at an overhanging support joint configured to rotate the overhanging support in a plane of the overhanging support, or a base pivot at a base joint configured to raise or lower the base.

15. The ultrasound system of claim 9, wherein the base comprises a stabilizing weight configured to balance with a weight of the overhanging support while the overhanging support extends away from the off-center vertical support.

16. The ultrasound system of claim 9, wherein the ultrasound display has a weight configured to balance a weight of the off-center vertical support while the overhanging support extends away from the off-center vertical support.

17. The rollstand of claim 1, wherein a length of the boom arm is adjustable.

18. The rollstand of claim 1, wherein the boom arm is rotatable about a vertical axis with respect to the base.

19. The rollstand of claim 1, wherein the off-center vertical support is rotatable about its longitudinal axis with respect to the base.

* * * * *